United States Patent [19]

Browner et al.

[11] Patent Number: 4,924,097
[45] Date of Patent: May 8, 1990

[54] MONODISPERSE AEROSOL GENERATOR FOR USE WITH INFRARED SPECTROMETRY

[75] Inventors: Richard F. Browner, Atlanta; James A. de Haseth, Athens, both of Ga.

[73] Assignees: Georgia Tech RSS. Corp, Atlanta; Univ of Ga Rss. Foundation, Athens, both of Ga.

[21] Appl. No.: 229,641

[22] Filed: Aug. 8, 1988

Related U.S. Application Data

[63] Continuation-in-part of Ser. No. 841,324, Mar. 19, 1986, Pat. No. 4,762,955, which is a continuation-in-part of Ser. No. 623,711, Jun. 22, 1989, Pat. No. 4,629,487.

[51] Int. Cl.$^{5}$ .......................... G01J 1/00; G01J 3/44; G01N 1/00

[52] U.S. Cl. ...................................... 250/343; 356/38; 356/301; 250/282

[58] Field of Search .......................... 356/36, 38, 301; 250/288, 282, 343; 261/78.2

[56] References Cited

U.S. PATENT DOCUMENTS

| | | | |
|---|---|---|---|
| 2,535,730 | 12/1950 | Gadret | 261/78 A |
| 2,785,923 | 3/1957 | Hickman | 239/434 |
| 2,887,181 | 5/1959 | Dillon | 261/782 |
| 2,966,312 | 12/1960 | Wilson et al. | 261/782 |
| 3,421,692 | 1/1969 | Babington et al. | 261/782 |
| 3,633,027 | 1/1972 | Ryhage | 250/288 |
| 3,639,757 | 2/1972 | Caroll et al. | 250/288 |
| 3,997,298 | 12/1976 | McLafferty et al. | 73/611 C |
| 4,055,987 | 11/1977 | McFadden | 250/288 |
| 4,066,411 | 1/1978 | Fine et al. | 73/611 C |
| 4,112,297 | 9/1978 | Miyagi et al. | 250/288 A |
| 4,181,437 | 1/1980 | Rossiter | 356/36 |
| 4,201,469 | 5/1980 | Matovsek et al. | 356/36 |
| 4,206,160 | 6/1980 | Suddendorf et al. | 261/78 A |
| 4,209,696 | 6/1980 | Fite | 250/288 |
| 4,213,326 | 7/1980 | Brodasky | 250/288 |
| 4,243,396 | 1/1981 | Cronenberg | 261/78.2 |
| 4,268,460 | 5/1981 | Boiarski et al. | 261/78.2 |
| 4,281,246 | 7/1981 | White et al. | 250/282 |
| 4,298,795 | 11/1981 | Takeuchi et al. | 250/288 |
| 4,300,044 | 11/1981 | Iribarme et al. | 250/288 |
| 4,330,490 | 5/1982 | Higgins | 239/434 |
| 4,358,302 | 11/1982 | Dahneke | 250/288 |
| 4,391,778 | 7/1983 | Andresen et al. | 250/288 |
| 4,403,147 | 9/1983 | Melera et al. | 250/288 A |
| 4,442,353 | 4/1984 | Baubron | 250/288 |
| 4,531,056 | 7/1985 | Lawowsky et al. | 250/281 |
| 4,570,068 | 2/1986 | Sakairi et al. | 250/288 A |
| 4,629,478 | 12/1986 | Browner et al. | 250/288 A |
| 4,667,100 | 5/1987 | Lagna | 250/288 |
| 4,687,929 | 8/1987 | Browner et al. | 250/282 |
| 4,762,955 | 8/1988 | Browner et al. | 250/288 A |

OTHER PUBLICATIONS

Willoughby, R. C. and R. F. Browner, Anal. Chem., 56, 2626 (1984).
Griffiths et al., Anal. Chem., 58, 1349A (1986).
Shafer, K. H. and P. R. Griffiths, Anal. Chem., 58, 3249 (1986).

*Primary Examiner*—Constantine Hannaher
*Assistant Examiner*—J. Eisenberg
*Attorney, Agent, or Firm*—Hurt, Richardson, Garner, Todd & Cadenhead

[57] ABSTRACT

A monodisperse aerosol generator forms a stable jet of liquid at a velocity allowing columnar breakup into droplets of uniform size and spacing. To prevent degradation of the monodisperse aerosol, it is disposed by entrainment in a high velocity gaseous stream. To provide an interface for direct injection onto a particle collection device or into an infrared or Raman spectrometer or to interface a liquid chromatograph with a particle collection device or an infrared or Raman spectrometer, the generator is followed by a desolvation chamber operation at about atmospheric pressure and a multistage pressure reducer which evacuates solvent vapor and gaseous medium to form a high momentum, solvent-depleted solute aerosol beam which is input into the infrared or Raman spectrometer.

14 Claims, 4 Drawing Sheets

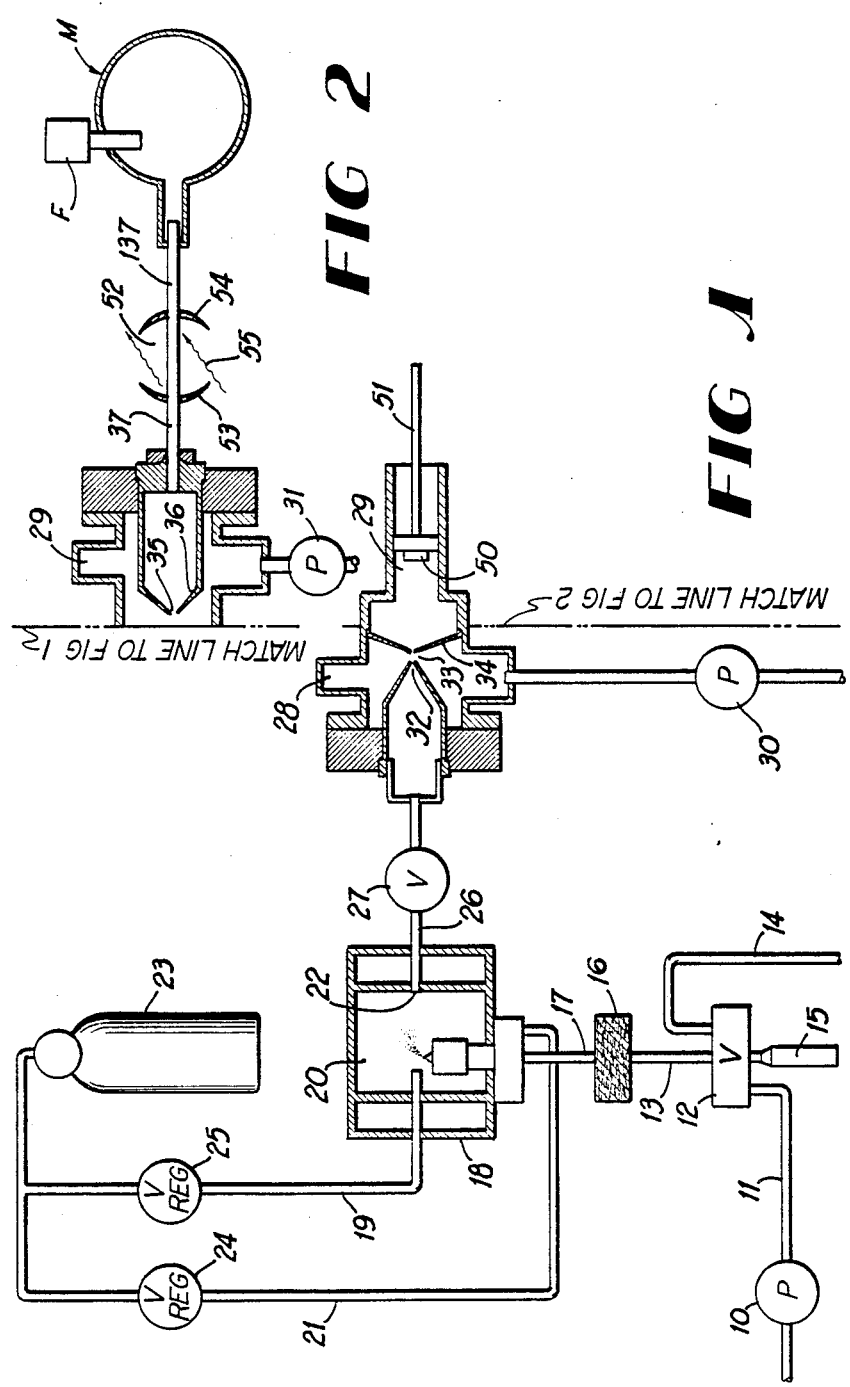

MONODISPERSE AEROSOL GENERATOR FOR USE WITH INFRARED SPECTROMETRY

BACKGROUND OF THE INVENTION

This invention is a continuation in part of prior application Ser. No. 841,324, filed Mar. 19, 1986, now U.S. Pat. No. 4,762,955, issued Aug. 9, 1988, which was a continuation-in-part of application Ser. No. 623,711, filed June 22, 1984, now U.S. Pat. No. 4,629,487, issued Dec. 16, 1986, and relates to a monodisperse aerosol generator and interface structure for forming an aerosol beam and introducing it into an infrared spectrometry apparatus or Raman spectrometry apparatus.

The monodisperse aerosol generator has separate utility aside and apart from the interface structure inasmuch as it may be used as a primary aerosol standard for reference purpose, as a source of injection of uniform particles to internal combustion devices, and as a source of sample solution introduction in flame and plasma atomic spectrometry (e.g., atomic absorption, atomic emission and atomic flouorescence spectroscopy). The monodisperse aerosol generator is, however, primarily intended for use as a means of solution introduction to a device acting as an interface between a liquid chromatograph and a particle collection apparatus or an infrared or Raman spectrometer, or for direct introduction of sample solutions to the interface without the use of the liquid chromatograph. The preferred interface structure according to this invention accepts the monodisperse aerosol and desolvates it to form a solute aerosol beam which, with high purity, is introduced into a particle collection apparatus or an infrared or Raman spectrometer.

The device is intended to provide a source of aerosol particles with a narrow Particle size distribution, and with a high degree of efficiency. It will be capable of producing aerosols from a wide range of liquids of varying physical properties. These liquids will include water and solutions of substances soluble in water, organic solvents, and solutions of substances soluble in organic solvents. The device will produce a stable aerosol, such that the aerosol, once formed, will show little tendency to coagulate to form agglomerates of particles. The aerosol will, however, be capable of controlled evaporation for Partial or complete removal of solvent. The size of the aerosol droplets will be controllable by simple means.

The device will be capable of producing a uniform and reproducible concentration of droplets in the gas stream over an extended period of time. It will also be capable of generating droplets with a wide range of selected sizes, covering a range typically of 5-200 micrometers diameter.

Liquid chromatography, particularly modern high performance liquid chromatography, provides a powerful tool for the separation of complex mixtures of either organic or inorganic species into their components. Such compounds may be thermally unstable or involatile under normal gas chromatographic conditions. Many organic compounds, including those of biological significance, and most ionic and inorganic compounds fall in this category.

Infrared and Raman spectrometry are widely used techniques for identifying and measuring concentrations of compounds in gases, many liquids, and solids./*

*Chemical Engineer's Handbook, 22-31, Perry, ed. (4th ed. 1963).

In a liquid chromatograph, a stream of solvent, containing a mixture of chemical species in solution, is passed at elevated pressure through a chromatographic column. The column is so designed that it separates the mixture, by differential retention on the column, into its components. The different components then emerge from the column as distinct bands in the solvent stream, separated in time. The liquid chromatograph provides, therefore, an ideal device for the introduction of single species separated from initially complex mixtures into an infrared or Raman spectrometer.

In order for the species emerging from the column to be introduced into a particle collection apparatus or an infrared or Raman spectrometer, partial or total removal of solvent from the dissolved species is desirable. This serves the purpose of limiting the species collected on collecting surfaces or interacting with the infrared beam. With extraneous species collected on collecting surfaces or interacting with the infrared beam, hybrid and less well characterized infrared or Raman spectra are produced. These types of infrared or Raman spectra are generally of diminished value for unknown compound identification.

One purpose of the invention is to provide a means of collecting small samples of substances as trace spots on a moving collection surface, such as a rotating disk or a linear collection cylinder. The trace spots may be interrogated directly so as to create a real-time infrared or Raman spectrum of the composition of the chromatographic effluent. Alternatively, the collection surface may be removed from the system and the trace spots examined outside the system (i.e., off-line) with an infrared or Raman spectrometer.

Another purpose of the invention is to provide a means of directly interacting small samples of substances in the form of particle beams with an infrared beam in a specially designed cell. The infrared beam interacts with the particle beam and Produces an infrared or Raman spectrum by direct particle/radiation interaction.

A further purpose of the invention is to provide a means of introducing the particle beam exiting the specially designed infrared beam interaction cell into a mass spectrometer. The infrared or Raman spectrometer/mass spectrometer acts as a combination system and provides a check on the results of the infrared spectrometer and as an additional sample element spectrum generator.

An additional purpose of the invention is to provide a means for a combination infrared or Raman spectrometer/particle collection system in which the particle beam exiting the specially designed infrared beam interaction cell is collected as small samples of substances as trace spots on a moving collection surface. This record can be examined outside the system with an infrared or Raman spectrometer or stored for examination at a later date.

Specifically, preferred goals of the invention are: (1) to allow direct, simple interfacing between the liquid chromatograph and the particle collection apparatus or the infrared or Raman spectrometer; (2) to provide efficient species transport between the liquid chromatograph and the particle collection apparatus or the infrared or Raman spectrometer; (3) to allow the use of all normal modes of ionization typically used for gas chromatography/infrared spectrometry; (4) to allow operation with a wide variety of solvents, (this would include solvents and solvent mixtures commonly used in normal, reversed phase and ion exchange liquid chromatograph—e.g., alcohols, nitriles, and aqueous buffers together with mixtures of same); (5) to produce sufficiently high species enrichment in the liquid chromatography effluent, by solvent removal, that the desolvated species may be gathered on collection surfaces as high purity trace spots, or may be introduced directly to the infrared beam interaction cell of a conventional infrared or Raman spectrometer; (6) to allow for a method of rapid infrared or Raman spectrometric analysis without the need for collecting analyte off line; (7) to be capable of reliable, routine operation; (8) to be capable of providing precise, quantitative analysis of species over at least two orders of magnitude infrared range.

Previous methods for generating uniform aerosols directly from liquid streams have worked on the principle of applying a regular external disturbance to a liquid cylindrical jet. The disturbance has been applied either axially or longitudinally to the jet as it emerges from a uniform circular nozzle. The disturbance has been provided by an electromechanical device, such as a piezoelectric crystal or a loudspeaker coil, driven by a high frequency power source.

The orifices used have either been laser-drilled steel or platinum disks, or fine bore stainless steel or glass capillary tubes. In general, the smallest droplets claimed for the devices are approximately 10 micrometers for circular disk orifices and 40 micrometers for capillary devices. A typical disk device is that of Berglund and Liu[1]. The liquid is passed under pressure through a disk orifice, emerging as a jet which is periodically disturbed by oscillations from a piezoelectric crystal. The Piezoelectric crystal is driven at a selected frequency by a radiofrequency generator. Stable and uniform aerosol production is only possible over a restricted range of liquid flow and oscillating frequency, for each particular orifice size. The initial aerosol stream is dispersed by a concentric gas jet, diluted with further air and neutralized electrically with a radioactive source, before emerging from the device.
[1] Berglund, R. N. and Liu, B. Y. H. Env. Sci. and Technology, 7, 147 (1973).

Capillary devices are typified by that of Lindblad and Schneider[2]. Here, liquid emerges from a stainless capillary tube, is subjected to transverse disturbances from a piezoelectric crystal under radiofrequency oscillations, and breaks into a uniform droplet stream. In general, the droplet density produced by the capillary type devices is lower than that produced by the disk devices, and so dilution gas for prevention of agglomeration is not used.
[2] Lindblad, N. R. and Schneider, J. M., J. Sci. Instrum., 42,635 (1965).

Other devices typically used for aerosol production, and suitable for use with a wide range of solvents and solutions are pneumatic nebulizers, fritted disk nebulizers and spinning disk nebulizers. Devices are also available which are based on ultrasonic aerosol production using focused-beam devices.

A number of approaches to interfacing liquid chromatography with infrared or Raman spectrometry have been attempted. However, all other devices which attempt to couple liquid chromatography with infrared or Raman spectrometry are incapable of use with solvents of high water content, and are incapable of running on-line with high water content solvents and require off-line collection techniques in order to obtain useful infrared or Raman spectra. For instance, the two prior methods had to be investigated off-line, the samples had to be completely devoid of water, and the contribution of the solvent had to be removed either by spectral subtraction or by evaporation before analysis of the solute.

The fritted disk nebulizer[3] is another nebulizing device which produces a fine, uniformly sized aerosol. In this device, liquid passes over the surface of a porous fritted disk or array of narrow bore tubes, through which gas emerges. The interaction of gas with liquid produces the aerosol. Limitations of the device for chromatographic coupling include severe memory effects, which result in peak broadening and loss of resolution, and also the need to use low liquid flows, typically less than 0.1 ml/minute.
[3] L. R. Layman and F. E. Lichte, Analytical Chemistry, 54, 638 (1982).

In the first method, the sample coming out of the liquid chromatograph was sprayed through a nebulizer which evaporated 80–90% of the solvent. The solute was then deposited on a suitable substrate, such as a conventional KBr collection plate or a rotating reflective surface, for off-line infrared analysis. However, if the solvent contained water, the remainder of the water had to be removed, generally through heating, as water dissolves the KBr substrate. Additionally, any other solvent left in the sample showed up as solvent absorption bands on the infrared analysis. Therefore, it was necessary to remove substantially all of the carrier solvent before subjecting the sample to infrared analysis in order to obtain unambiguous results[4].
[4] Biemann, K. and J. Gagel, Continuous Infrared Spectroscopic Analysis of Isocratic and Gradient Elution Reversed-phase Liquid Chromatography Separations, 59 Anal. Chem. 1266 (1987).

In the second method, the sample coming out of the liquid chromatograph was dripped into a collection cup or a train of collection cups filled with packed KBr. The solvent was evaporated from the sample, generally by heating, and the analysis was affected in situ diffuse reflectance. This method has the same drawbacks as the first method; it must be done off-line, all water must be removed, and the presence of any solvent can taint the results by masking the spectrum. Additionally, any heating of the sample has the potential to alter the sample and to produce erroneous infrared analysis[5].
[5] Griffiths, P. et al., The Hyphenation of Chromatography and FT-IR Spectrometry, 58 Anal. Chem. 1349A (No. 13, Nov. 1986).

In gas chromatography/Fourier transform infrared spectrometry systems, the sample is heated to 200° to 300° C. in the chromatograph. The spectra can be collected as effluent leaves the chromatograph or after deposition on a cryogenically cooled surface. The surface is then placed under the infrared beam for spectral generation.

In the present invention, using the aerosol generator described in detail below presents at least two distinct advantages. First, there is no need to heat or cool the samples, eliminating the potential that the compound will decompose under non-ambient conditions. Second, there are significantly more compounds which can be analyzed by liquid chromatography that cannot be analyzed by gas chromatography, including those which are involatile or thermally labile.

The present invention obviates these disadvantages and provides several additional advantages in the continuous on-line infrared or Raman spectral analyses of liquid chromatographic components using organic or water-based solvents. First, the invention allows for an on-line analysis of the components, either by analysis of particles collected on a moving surface or by direct interaction of the infrared beam with the solute particle stream. Second, the invention allows for the analysis of solute from a solution using any solvent, including those with a high percentage of water, without the need for heating to eliminate the solvent. Third, the particle beam can be collected on a suitable collection surface, such as KBr, immediately upon exiting the interface of the invention without the risk of damage t the surface.

No relevant prior art is known with relation to any monodisperse aerosol generator per se.

BRIEF DESCRIPTION OF THE DRAWING FIGURES

FIG. 1 is a schematic view of the present invention in use as a particle collection system;

FIG. 2 is a schematic view with a match line to FIG. 1 of the invention in use as a combination infrared spectrometer/mass spectrometer system;

DETAILED DESCRIPTION OF THE INVENTION

FIGS. 1 and 2 illustrate that form of the invention forming an interface for use in a liquid chromatography or direct injection to a particle collection system or a direct infrared beam/particle beam interaction, respectively. The relatively pulseless pump 10 of the liquid chromatography system pumps effluent eluted from the chromatograph column (not shown) into the line 11 in which an optional multi-port sample valve 12 may be interposed. In the combined system, sample injection is not used but provision may be necessary to reduce the flow through the outlet line 13 and, for this purpose, split flow may be adjusted with part of the effluent being directed over the line to waste or to suitable collection means. For direct injection, the pump 10 may pump only solvent in the line 11 and the sample may be introduced a by the syringe 15.

Figure 5:
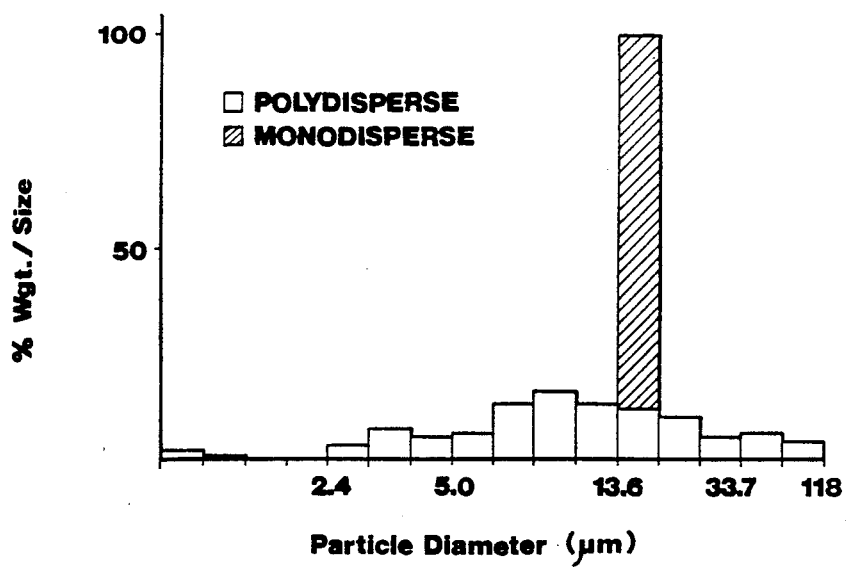
FIG. 5 is a graph comparing monodisperse and polydisperse aerosols as referred to herein.

In any event, the solution is filtered at 16 before passing through the line 17 to the monodisperse aerosol generator 18. Although "monodisperse" implies a single aerosol droplet or particle size, that term is used herein to mean droplets or particles which have a very narrow range of sizes. The meaning should be clear from FIG. 5 wherein typical monodisperse aerosol within the meaning herein is compared with a polydisperse aerosol. The polydisperse aerosol illustrated in FIG. 5 was generated from a Perkin-Elmer cross flow pneumatic nebulizer whereas the monodisperse aerosol was generated according to this invention using a 6 mm orifice, as will be described presently. The measurements from which FIG. 5 was generated were of Fraunhofer diffraction from the aerosols generated.

As will be explained more fully hereinafter, the monodisperse aerosol is entrained in a high velocity gas jet emanating from the capillary 19 and is directed into the confined space 20 for the purpose of desolvation. The aerosol is suitably diluted with sheath gas entering from the line 21 in amount sufficient to maintain the desolvation chamber space 20 substantially at atmospheric pressure. The use of substantially atmospheric pressure in the chamber 20 greatly enhances the desolvation process and allows the monodisperse aerosol droplets or particles to be substantially completely depleted of the solvent so that by the time the aerosol reaches the outlet orifice 22 it is in the form of solvent-depleted solute.

The dispersion and sheath gases preferably are inert such as argon or helium from a suitable supply 23. Their rates of flow over the line 21 and to the capillary 19 may be adjusted by the respective flow regulators 24 and 25.

The chamber 20 may typically be 40 mm in diameter and approximately 30 cm long. The outlet tube 26 may be ¼ inch stainless steel tube provided with a suitable shut-off valve 27 to isolate the relatively high pressure chamber 20 from the vacuum region.

The vacuum region is shown as comprised of the two chambers 28 and 29 connected to the respective pump 30 and 31. Typically the pump 30 evacuates the chamber at a rate of about 300 liters per minute to maintain the chamber 28 at a pressure in the range of 2-20 torr where the pump 31 typically evacuates about 150 liters per minute to maintain the chamber 29 at a pressure in the range 0.01 to 10 torr.

The nozzle end 32 of the tube 26 is precisely aligned with the conical end 33 of the cone skimmer 34 forming the first skimmer. The separation between 32 and 33 typically may be about 1–3 cm. In the particle collection mode (FIG. 1) the separation between the nozzle end 35 of the second cone skimmer 36 and the rotating collection plate 50 and support disk 51 may be in the 1–10 cm range. In the infrared radiation/particle interaction mode (FIG. 2) the separation between the nozzle end 35 and the flat end 36 of the outlet tube 37 may be in the 5–15 cm range.

With the internal diameter of the nozzle 32 being 0.5 mm whereas the internal diameters of the two skimmers 33 and 36 and also of the nozzle 35 being 1.0 mm optimum results were obtained as were also obtained by using 0.5 mm inside diameters for all but the skimmer 33 whose inside diameter was 1.0 mm.

OPERATION OF THE SYSTEM

1. Particle Collection Mode a. Direct Injection Mode

In this mode of operation, a constant flow of solvent is supplied to the monodisperse aerosol generator 18 with the low-pulse liquid pump 10. The monodisperse generator produces a finely dispersed solvent aerosol which passes, together with the dispersion gas, into the desolvation chamber 20. In the desolvation chamber, the majority of the solvent evaporates. The combination of dispersion gas and solvent vapor then passes sequentially through the first pressure reduction chamber 28 where some of the mixture of dispersion gas and solvent vapor is removed by vacuum pump 30. The remainder of the mixture of dispersion gas and solvent vapor is removed in the combination pressure reduction/collection plate chamber 29 by vacuum pump 31.

Samples are introduced to the system by means of an injector 15. The sample may be either a pure liquid, or consist of a solution of solid or liquid in a suitable solvent. The injector may be either a multi-port valve, a septum injection system, or a high performance liquid chromatography auto-injector system. Generally, a small sample volume (typically 5-100 microliters) is introduced, which might typically contain a few micrograms or nanograms of the substance to be analyzed. The aerosol generated by the monodisperse generator now passes through the desolvation chamber and the first pressure reduction/skimmer chamber which skims off the particle beam from the gas stream, enriching the particle beam. However, when sample is present in the solvent stream, a highly dispersed aerosol of sample material remains after solvent evaporation. The particle beam then passes to a second chamber where the pressure is reduced further and the particles are collected on the collection plate as a small spot whose diameter is approximately equal to the diameter of the skimmer in the momentum separator (typically 0.1 to 2.0 mm depending on the choice of an appropriate skimmer diameter and skimmer configuration). This spot may be interrogated directly for a real-time infrared or Raman spectra of the chromatogram or the collection surface may be removed and examined off-line with an infrared or Raman spectrometer. The separation of the particle beam from the gas stream is effective because the supersonic expansion which occurs through the skimmer of the interface imparts sufficient momentum to the aerosol particles so that they are largely unaffected by the pumps in the two chambers 28, 29.

b. High Performance Liquid Chromatograph Mode

Operation of the interface with a high performance liquid chromatograph is very similar to operation with the direct injection device described in the previous section. The only substantial difference is that the sample may now contain a mixture of compounds, which are separated into individual compounds by passage through a chromatography column (not shown) placed between the injector valve and the aerosol generator.

2. Infrared Radiation/Particle Interaction Mode

Operation of the interface in the infrared radiation/particle interface (IR/PI) mode in the direct injection mode and the high performance liquid chromatograph modes is very similar to the operation of the interface in the particle collection mode in the direct injection mode and the high performance liquid chromatograph mode. The substantial difference is that now the sample after leaving the desolvation chamber passes through two pressure reduction chambers 28, 29 and out through an outlet tube 37 and into a cell 52. In this cell, the infrared beam 55 is focused by two mirrors 53, 54 so as to interact directly with the particle beam. An infrared spectrum is then produced by direct particle/radiation interaction. This mode does not require any particle collection and allows the rapid generation of infrared spectral data.

3. Combination Infrared Spectrometer/Mass Spectrometer Mode

Operation of the combination infrared spectrometer/mass spectrometer (IR/MS) system is very similar to operation of the IR/PI mode with the only substantial difference being a dual spectrometer system in which a mass spectrometer M is connected to the infrared beam interaction cell 52 by an extension outlet tube 137.

4. Combination Infrared Spectrometer/Particle Collection Mode

Operation of the combination infrared spectrometer/particle collection (IR/PC) system is very similar to operation of the IR/PI mode with the only substantial difference being the addition of a particle collection system 56 connected to the infrared beam cell 52 by an extension outlet tube 137. The particle collection plate 50 can be examined off-line or stored for later examination.

Figure 3:
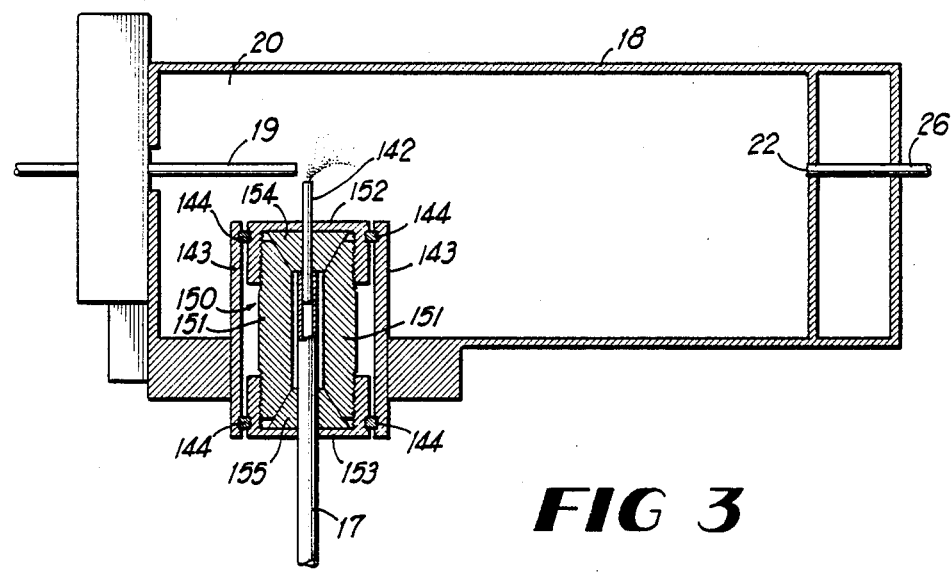
FIG. 3 is a sectional view through a monodisperse aerosol generator according to the invention.

FIG. 3 illustrates the preferred nebulizer or monodisperse aerosol generator according to this invention. As shown, the housing of the generator is provided, having a glass tube connection 22 for connection to the desolvation chamber (FIG. 1), for containing the nebulizer. The nebulizer structure comprises the hollow tube 142 seated in the retaining gasket 154 in body 151 and held in place by the cap 152 threaded onto the body 151 as shown. Line 17 enters body 151 through retaining gasket 155 and held in place by the cap 153. The entire body structure is connected to the monodisperse aerosol generator 18 by gaskets 144 between caps 152 and 153 and support column 143. The solution is pumped through the line 17 previously described and causes same to issue a stable jet from the tip of the tube 142.

Figure 4:
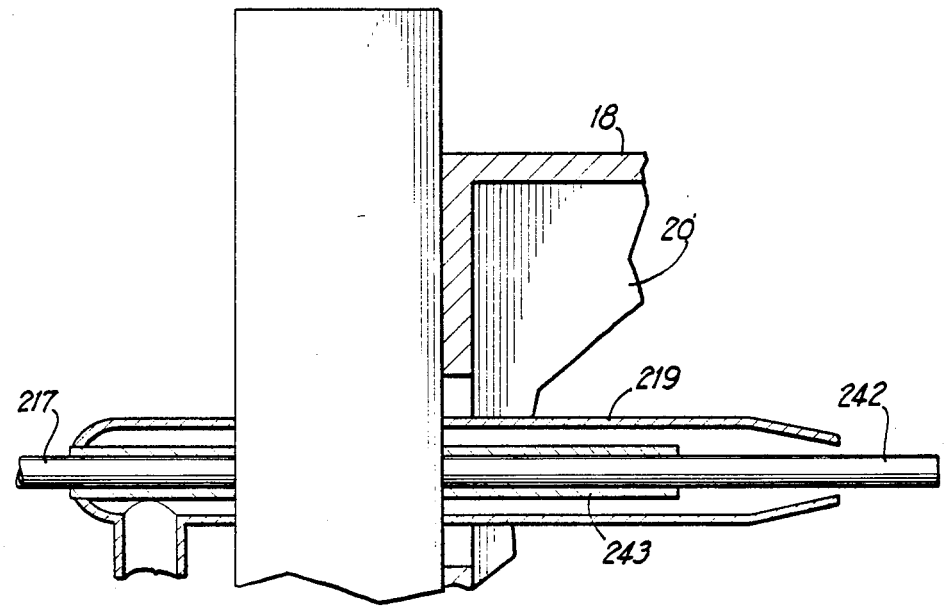
FIG. 4 is a sectional view through an alternate embodiment monodisperse aerosol generator using a coaxial gas/liquid injection system.

FIG. 4 illustrates an alternate embodiment nebulizer or monodisperse aerosol generator. As shown, the nebulizer structure comprises the hollow tube 242 supported by retaining tube 243, both located within and coaxial to tube 219. The solution is pumped through the line 217 and causes same to issue a stable jet from the tip of tube 242 which mixes with the gas jet issued from tube 219. In this embodiment, the gas jet within tube 219 acts as a self-centering device for tube 242 within tube 219.

Figure 6:
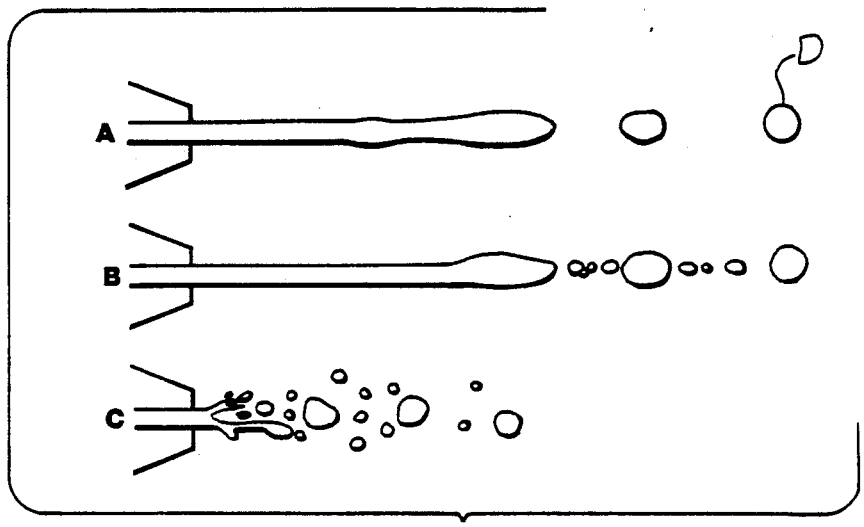
FIG. 6 illustrates columnar breakup (A) according to this invention in comparison to sinuous breakup (B) and atomization (C)
Figure 7:
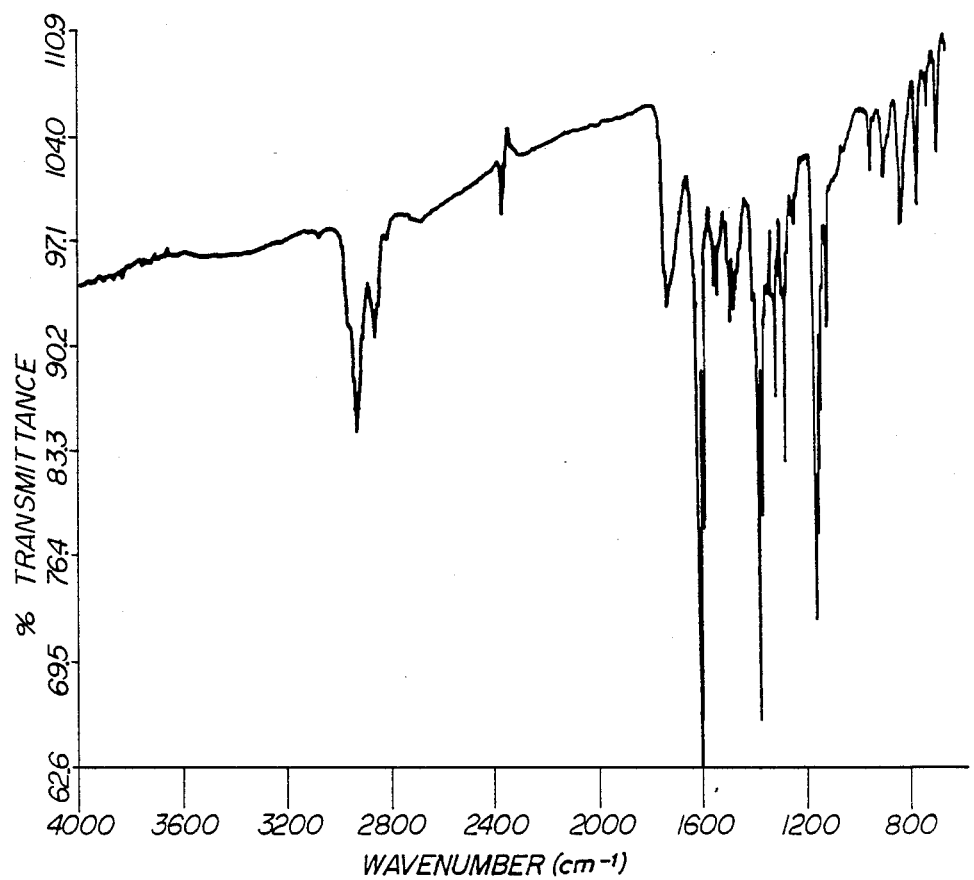
FIG. 7 is a Fourier transform infrared spectrum using the Particle Collection mode.

Although the diameter of the nozzle orifice may range between about 2 to about 100 micrometers, the range of about 9 to about 20 micrometers is preferred. The stable jet is controlled as to its velocity so that it is subjected to the columnar breakup as indicated in FIG. 6 at A. Progressively higher velocities are depicted at B and C which respectively illustrate sinuous breakup and atomization.

The columnar or monodisperse breakup of A is Rayleigh breakup and produces droplets or particles D of substantially uniform size and spacing, the droplet diameters being about two times the orifice diameter. Generally speaking, with the preferred orifice diameters, the stable jets with Rayleigh breakup were produced with flow rates below about 3 mL/min.

The glass nebulizer tip is constructed from thick walled glass capillary tubing of approximately 0.25 inches external diameter. One end of the tube is initially flame sealed, to give a conical closure to the tube. This end is then opened, by grinding with a fine abrasive medium (such as 400 grade silicon carbide paper), until an orifice of suitable diameter has been created. The diameter of the orifice may be measured using a calibrated microscope. The other end of the tube is formed into a lip, which is ground on its lower edge to form a liquid-tight seal against the gasket place in the threaded end of the metal block. The nebulizer tip is held in place with the retaining cap.

The liquid supply to the device comes from a pump, capable of sustaining liquid flows in the range of 0.01 mL/min.—3 mL/min., at pressures up to approximately 300 pounds per square inch. The pump should also provide little pressure pulstation in operation. A typical Pump used is one suitable for High Performance Liquid Chromatography.

Dispersion gas is introduced from a capillary tube 19, constructed from stainless steel or some other suitable rigid material. The dispersion gas tube is positioned with suitable alignment devices, to be fixed at between 3 and 10 mm above the tip of the glass orifice 142. Dispersion gas, controlled by suitable means such as pressure controllers, needle valves and rotameters, flow through the dispersion gas capillary at a flow adequate to produce efficient dispersion of the aerosol Flows will typically be in the range of 0.5 to 2 L/min. of gas.

The aerosol produced by the device may be sampled by any appropriate means, or pass into a desolvation chamber or sampling port of another device by sealing the aerosol generation device into a closed chamber. This first chamber may then be sealed to subsequent devices, to ensure efficient transfer of the aerosol to these devices.

The primary differences between this device and previous devices, and the advantages resulting from these, are the following:

(1) No source of external mechanical disturbance is needed for the operation of the device.

(2) The orifice may be readily constructed from glass capillary tubing, to produce highly circular openings of 2 micrometers diameter and above.

(3) The diameter of the aerosol produced by the device is controlled by the diameter of the liquid orifice. The aerosol particle diameter is approximately 1.2 x the orifice diameter. The precise relationship between aerosol diameter and orifice diameter is dependent on the compressibility of the liquid.

(4) The selection of aerosol diameter, by interchange of orifices, may be accomplished readily and rapidly.

(5) The device operates very stably over extended periods of time without the need for adjustment.

(6) The device operates very reproducibly from day to day, without the need for realignment of components, or the re-optimization of parameters, between runs.

(7) A wide variety of liquids may be used with the device, requiring only that the contents of the liquid reservoir be changed in order to change the liquid to be converted to an aerosol. Both water, organic solvents, mixtures of water and organic solvents, and mixtures organic solvents may be used with the device.

(8) Inorganic and organic species may be dissolved in any of the solvents or solvent mixtures mentioned in item (7) at concentrations up to 1% by weight of dissolved solids, without blockage problems occurring in the device.

(9) A wide variety of solvents may be used, including 100% water, without the need for heat nebulizers, ambient solvent evaporation, or heat solvent evaporation, even when using KBr collection plates.

(10) Continuous, on-line infrared or Raman spectral analysis can be performed without the need to remove collection plates or to interrupt the process for off-line analysis.

(11) The particle collection plate, if used instead of or in conjunction with the light tube, can be saved as a "hard copy" of the spectrum.

(12) The conical skimmer design of the interface improves the efficiency of the solvent and carrier gas removal process by about 10 times over prior designs.

(13) The spectra developed can be compared to a computerized spectra reference base to identify the sample spectra.

(14) The generally solvent-free particle beam has small dimensions on the order of 0.1 to 2.0 mm diameter which allows for a greater number of sample spots to be collected on the collection plates.

(15) The low pressure in the collection chamber improves the collection on the collection surface by reducing the air boundary layer on its surface.

(16) Solvent water is eliminated so efficiently that alkali halide collection plates may be used without the water dissolving the alkali halide plate.

(17) The particle beam deposits small diameter sample spots on the alkali halide plate without the necessity of manually placing dried samples on the alkali halide plate.

It will be appreciated that to prevent degradation of the monodisperse aerosol generation due to coagulation and/or impact between droplets, the dispersion must be effected near the point of random or Rayleigh breakup, by dispersing the aerosol preferably either coaxially, or at an angle, preferably about 90°, to the axis of the stable jet. It will also be appreciated that the vacuum means continuously evacuates gaseous medium solvent vapor and solvent-depleted solute, while separating off the solvent vapor and gaseous medium and form the monodisperse aerosol beam of solvent-depleted solute. This beam has high momentum and Passes through the final skimmer into the ion source. It should also be understood that the solvent-depleted solute beam consists of particles of smaller size than those of the originally generated aerosol and contains a somewhat greater relative size range of distribution.

It should also be noted that this invention serves two very distinct purposes: (1) as a novel source of monodispersed particles, which would have potential applications in the area of aerosol calibration and particle generation, and (2) the interface between a flowing liquid stream and a particle collection device or a Fourier transform infrared or near infrared Fourier transform Raman spectrometer, or Hadamard transform infrared spectrometer, or Hadamard transform near infrared Raman spectrometer. Although the interface contains the aerosol generator, the combination of physical processes to remove solvent from the droplets and enrich the solute particles is also critical for the performance of the interface.

The aerosol generation/desolvation device developed for the mass spectrometry application produces a stream of dry monodispersed particles which in this invention either are collected with high efficiency and very little beam spreading onto a collection device for interrogation by an infrared beam, or are passed though a cell for interaction with the infrared beam producing an immediate infrared spectral analysis. This invention is also the only known device which allows on-line production of Fourier transform infrared spectra or Fourier transform Raman spectra, or Hadamard transform infrared spectra or Hadamard transform Raman spectra from both polar and non-polar solutions.

What is claimed is:

1. A method of introducing solute into an infrared or Roman spectrometer, which comprises the steps of:
   (a) providing a solution including a relatively volatile solvent and a relatively involatile solute;
   (b) generating an aerosol from the solution by delivering the solution through a conduit at a velocity such that formation of droplets with a narrow size distribution occurs;
   (c) providing a dispersing gas;
   (d) dispersing the formed droplets with the gas;

(e) entraining the aerosol in gas and desolvating the aerosol at substantially atmospheric pressure;

(f) expanding the components of step (e) into low pressure environment while removing gas therefrom to form a high momentum aerosol beam of solute particles with a narrow particle size distribution; and (g) directing said beam into an infrared or Roman spectrometer.

2. A method as defined in claim 1, wherein said beam is directed onto a collection surface in the infrared or Raman spectrometer.

3. A method as defined in claim 1, wherein an infrared beam directly interacts with the beam of solute particles.

4. A method as defined in claim 3, wherein the beam of solute particles is subsequently directed onto a collection surface.

5. A method as defined in claim 1, wherein the beam of solute particles is subsequently directed from the infrared or Raman spectrometer into a mass spectrometer.

6. A method as defined in claim 1, wherein the solution is provided from the effluent of a liquid chromatograph.

7. A system for introducing solvent depleted solute into an infrared or Raman spectrometer which comprises:

(a) means for providing a solution including a relatively volatile solvent and a relatively involatile solute;

(b) means for generating a monodisperse aerosol from the solution by supplying the solution to a nozzle at a rate sufficient to produce a stable jet of liquid having a velocity such that monodisperse droplet breakup of the jet occurs;

(c) dispersing means for entraining the droplets after the point of droplet formation in a high velocity flow of gas so as to retain the monodisperse nature thereof;

(d) a desolvating chamber for producing the solvent depleted solute;

(e) pressure reduction means for expanding said gas with entrained droplets into a low pressure environment while removing gas therefrom to form a high momentum monodisperse aerosol beam of solute particles; and (f) means for directing said beam into an infrared or Raman spectrometer.

8. The system of claim 7 wherein said pressure reduction means includes a first vacuum chamber having a pressure in the range of 2-20 torr.

9. The system of the claim 7 where said pressure reduction means further comprises two vacuum chambers, the second having a pressure in the range of 0.01 to 10 torr.

10. The system of claim 7, wherein said desolvating chamber is maintained at about atmospheric pressure.

11. The system of claim 7, further comprising a vacuum chamber for continuously evacuating gaseous medium and a vacuum pump which maintains said vacuum chamber at a pressure in the range of 2-20 torr.

12. The system of claim 11, further comprising a second vacuum chamber and a second vacuum pump which maintains said second vacuum chamber at a pressure in the range of 0.01 to 10 torr.

13. The system of claim 7, further comprising a collection surface onto which the beam of particles is directed.

14. The system of claim 7, further comprising means for directing the particle beam from the infrared or Raman spectrometer into a mass spectrometer.

* * * * *

UNITED STATES PATENT AND TRADEMARK OFFICE
CERTIFICATE OF CORRECTION

PATENT NO. : 4,924,097
DATED : May 8, 1990
INVENTOR(S) : Browner, et al.

It is certified that error appears in the above—identified patent and that said Letters Patent is hereby corrected as shown below:

Column 10, line 60, replace "Roman" with --Raman--.

Signed and Sealed this

Twelfth Day of November, 1991

Attest:

HARRY F. MANBECK, JR.

*Attesting Officer*  *Commissioner of Patents and Trademarks*